US008727991B2

(12) United States Patent
Hasegawa-Johnson

(10) Patent No.: US 8,727,991 B2
(45) Date of Patent: May 20, 2014

(54) PROBABILISTIC SEGMENTAL MODEL FOR DOPPLER ULTRASOUND HEART RATE MONITORING

(75) Inventor: Mark Allan Hasegawa-Johnson, Champaign, IL (US)

(73) Assignee: Salutron, Inc., Fremont, CA (US)

( * ) Notice: Subject to any disclaimer, the term of this patent is extended or adjusted under 35 U.S.C. 154(b) by 223 days.

(21) Appl. No.: 13/220,162

(22) Filed: Aug. 29, 2011

(65) Prior Publication Data
US 2013/0053696 A1 Feb. 28, 2013

(51) Int. Cl.
A61B 8/02 (2006.01)

(52) U.S. Cl.
USPC ............................. 600/453; 600/407; 600/437

(58) Field of Classification Search
USPC .......................................... 600/453, 407, 437
See application file for complete search history.

(56) References Cited

U.S. PATENT DOCUMENTS

| 4,319,580 | A |   | 3/1982  | Colley et al.       |
|-----------|---|---|---------|---------------------|
| 4,357,944 | A |   | 11/1982 | Mauser et al.       |
| 4,848,355 | A |   | 7/1989  | Nakamura et al.     |
| 4,890,624 | A |   | 1/1990  | Ganguly et al.      |
| 5,156,154 | A |   | 10/1992 | Valenta, Jr. et al. |
| 5,213,104 | A |   | 5/1993  | Reynolds            |
| 5,377,684 | A |   | 1/1995  | Hara                |
| 5,839,105 | A |   | 11/1998 | Ostendorf et al.    |
| 6,024,705 | A | * | 2/2000  | Schlager et al. ............... 600/508 |
| 6,312,382 | B1|   | 11/2001 | Mucci et al.        |
| 6,544,180 | B1|   | 4/2003  | Doten et al.        |
| 6,626,838 | B2|   | 9/2003  | Doten et al.        |
| 6,782,362 | B1|   | 8/2004  | Hon et al.          |
| 6,843,771 | B2|   | 1/2005  | Lo et al.           |
| 7,216,079 | B1|   | 5/2007  | Barnard et al.      |
| 7,464,031 | B2|   | 12/2008 | Axelrod et al.      |
| 7,505,950 | B2|   | 3/2009  | Tian et al.         |
| 7,559,899 | B2|   | 7/2009  | Lo et al.           |
| 7,577,626 | B1|   | 8/2009  | Mountrakis          |
| 7,580,741 | B2|   | 8/2009  | Cazares et al.      |
| 2003/0163032 | A1| * | 8/2003 | Terry ............................ 600/322 |
| 2003/0163057 | A1|   | 8/2003 | Flick et al.        |
| 2005/0004486 | A1|   | 1/2005 | Glass et al.        |
| 2006/0015373 | A1| * | 1/2006 | Cuypers ............................ 705/4 |
| 2006/0282236 | A1| * | 12/2006| Wistmuller ....................... 703/2 |

(Continued)

FOREIGN PATENT DOCUMENTS

WO 2005107587 A2 11/2005

OTHER PUBLICATIONS

Choi et al., The Distribution of Refractory Periods Influences the Dynamics of Ventricular Fibrillation, 2001, Circulation Research—Journal of the American Heart Association, Circ Res. 2001;88:e49-e58, pp. 1-10.*

Primary Examiner — Tse Chen
Assistant Examiner — Vani Gupta
(74) Attorney, Agent, or Firm — Vierra Magen Marcus LLP

(57) ABSTRACT

A heart rate of a subject is determined using a probabilistic segmental model. Reflections of ultrasound signals from the subject, for instance, are down modulated to an audio band and velocity samples are obtained. For a signal analysis window of the samples, e.g., 25 msec. of samples, features of the samples are obtained. Based on the features, a first set of probabilities is obtained for different candidate current heartbeat periods. A second set of probabilities is determined based on combinations of different previous heartbeat periods. One of the candidate current heartbeat periods is determined to be most probable, based on the first and second sets of probabilities.

17 Claims, 10 Drawing Sheets

(56) References Cited

U.S. PATENT DOCUMENTS

| | | | |
|---|---|---|---|
| 2007/0244524 A1* | 10/2007 | Qu et al. | 607/88 |
| 2007/0288183 A1 | 12/2007 | Bulkes et al. | |
| 2009/0043216 A1 | 2/2009 | Lin et al. | |
| 2009/0171868 A1 | 7/2009 | Bottou et al. | |
| 2010/0049069 A1 | 2/2010 | Tarassenko et al. | |
| 2010/0056939 A1 | 3/2010 | Tarassenko et al. | |
| 2010/0081940 A1 | 4/2010 | McKenna | |
| 2012/0243707 A1* | 9/2012 | Bradley et al. | 381/98 |

\* cited by examiner

Fig. 4J
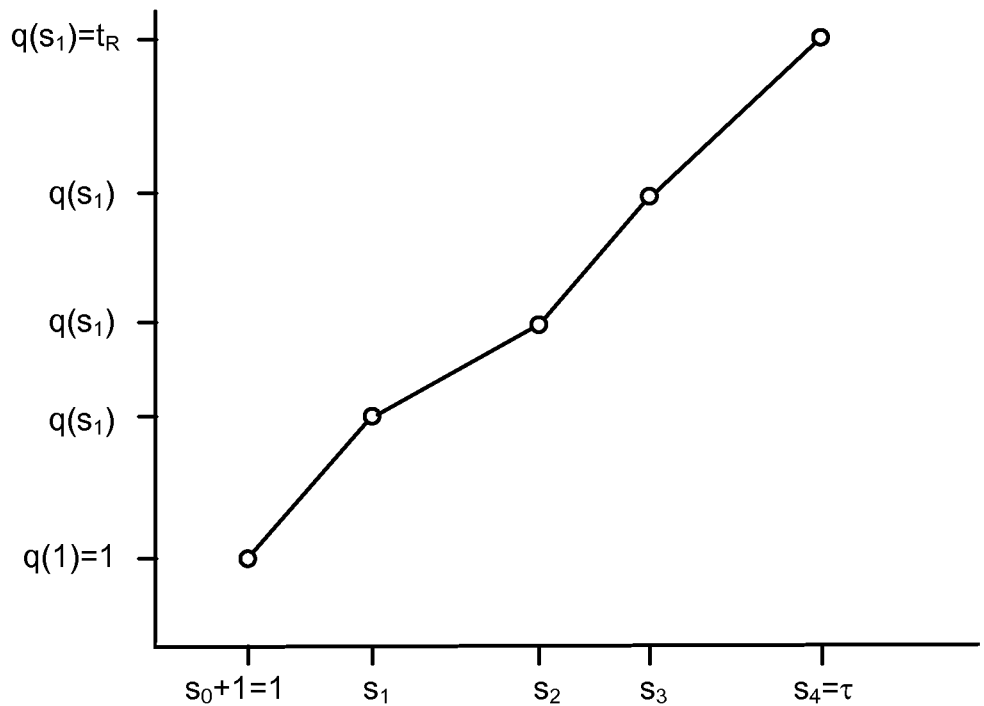
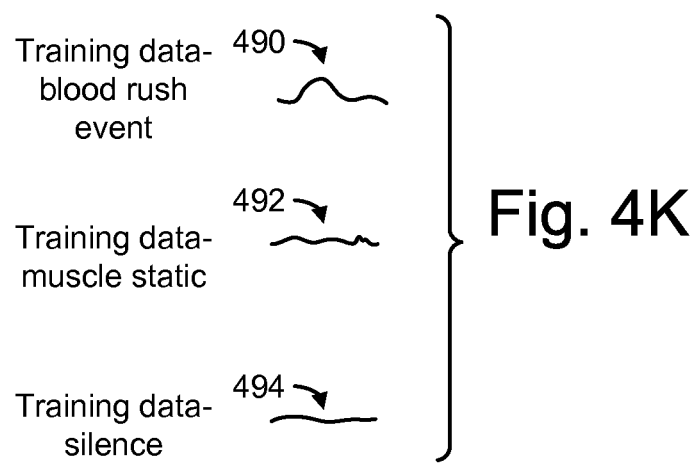
Fig. 4K

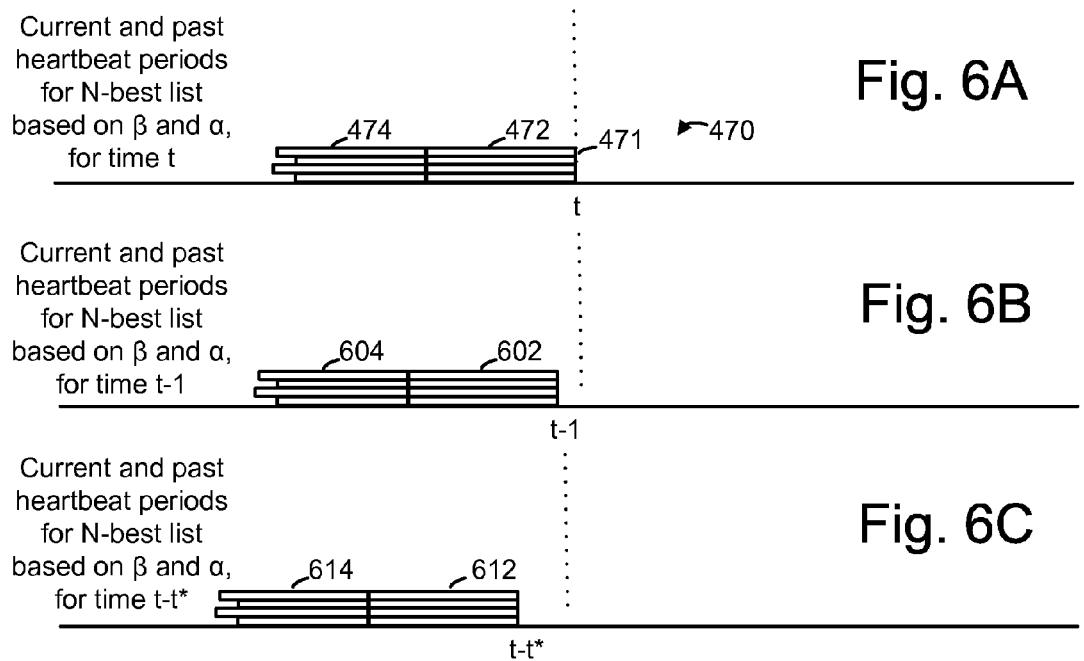

US 8,727,991 B2

PROBABILISTIC SEGMENTAL MODEL FOR DOPPLER ULTRASOUND HEART RATE MONITORING

BACKGROUND

Wireless heart rate monitors are commonly used during exercise, athletic competitions, medical tests and other activities. For example, a non-invasive heart rate monitor can be worn by a user, contacting the user at a suitable location such as the wrist. Invasive heart rate monitors, which are implanted in the body, can also be used. One example of a wrist-worn heart rate monitor transmits an ultrasonic signal toward the wrist and detects reflections of the signal from a blood vessel within the wrist. Based on the Doppler principle, a motion of blood in the vessel and/or the vessel itself can be detected and used to determine a heart rate of the subject. However, accuracy of the heart rate measurement can be impaired due to factors such as noise, muscle movement and low signal-to-noise ratio.

SUMMARY

In one embodiment, at least one tangible processor-readable storage device having computer readable software embodied thereon is provided for programming at least one processor to perform a method for monitoring a heartbeat period of a subject. The method includes obtaining velocity samples from a signal reflected from a subject, and determining features of the velocity samples. The method further includes, for each candidate current heartbeat period of different candidate current heartbeat periods, determining a first set of probabilities $\beta$ by determining probabilities of different current heartbeat periods, based on the features. The method further includes determining a second set of probabilities $\alpha$ by determining probabilities of the different current heartbeat periods, based on an integer number Nphb>0 of different previous heartbeat periods. The method further includes determining which of the candidate current heartbeat periods is most probable, based on the first and second sets of probabilities.

In another embodiment, a heartbeat period monitoring device is provided for monitoring a heartbeat period of a subject. The heartbeat period monitoring device includes at least one micro-controller, at least one transmitter which transmits a signal toward a subject, responsive to the micro-controller, at least one receiver which receives a reflection of the signal from the subject, and circuitry for down modulating the reflection of the signal to provide a signal in an audio band, responsive to the micro-controller. The at least one micro-controller: (a) obtains velocity samples from the signal in the audio band, (b) determines features of the velocity samples, (c) for each candidate current heartbeat period of different candidate current heartbeat periods, to determine a first set of probabilities $\beta$, determines probabilities of different current heartbeat periods, based on the features, (c) to determine a second set of probabilities a, determines probabilities of the different current heartbeat periods, based on an integer number Nphb>0 of different previous heartbeat periods, and (d) determines which of the candidate current heartbeat periods is most probable, based on the first and second sets of probabilities.

In another embodiment, a heartbeat period monitoring device is provided for monitoring a heartbeat period of a subject. The heartbeat period monitoring device includes at least one micro-controller, and at least one laser emitter diode package responsive to the at least one micro-controller. The at least one laser emitter diode package comprises a laser emitter diode and a monitor photodiode in a cavity, the laser emitter diode transmits a laser beam toward a subject, the laser beam is reflected by the subject, at least in part, back into the cavity as a reflected optical signal, the reflected optical signal mixes in the cavity to provide a mixed optical signal, the monitor photodiode converts the mixed optical signal to an electrical signal, and the electrical signal is in an audio band and has amplitude fluctuations with a frequency equal to a Doppler shift of the reflected optical signal. The at least one micro-controller: (a) obtains velocity samples from the electrical signal, (b) determines features of the velocity samples, (c) for each candidate current heartbeat period of different candidate current heartbeat periods, to determine a first set of probabilities $\beta$, determines probabilities of different current heartbeat periods, based on the features, (c) to determine a second set of probabilities $\alpha$, determines probabilities of the different current heartbeat periods, based on an integer number Nphb>0 of different previous heartbeat periods, and (d) determines which of the candidate current heartbeat periods is most probable, based on the first and second sets of probabilities.

Corresponding methods may also be provided, along with a tangible processor-readable medium which stores code which is executable by a microprocessor/microcontroller to perform the methods described herein.

BRIEF DESCRIPTION OF THE DRAWINGS

FIG. 4A depicts signal analysis windows of the portion 342 of the velocity signal of FIG. 3D.

FIG. 4B depicts a cepstrum signal x(t) formed from the signal analysis window 400 of FIG. 4A.

FIG. 4C depicts a discriminatively transformed vector z(t) formed from the cepstrum 430 of FIG. 4B.

FIG. 4D depicts example candidate current heartbeat periods $\tau$ used to determine segment likelihoods $\beta$ from the discriminatively transformed vector z(t) of FIG. 4C.

FIG. 4E depicts example current and two previous heartbeat periods used to determine period likelihoods $\alpha$.

FIG. 4F depicts a current and a previous heartbeat period of an N-best list for a time value of t, based on $\beta$ and $\alpha$.

FIG. 4G depicts an instantaneous heart rate formed from the N-best list of FIG. 4F.

FIG. 4J depicts a piece-wise linear mapping from the time axis of the signal, $1 \leq s \leq \tau$, to the time axis of the reference heartbeat model, $1 \leq q(s) \leq tR$.

FIG. 4K depicts example training data for one heartbeat period.

FIG. 6A repeats FIG. 4F, which depicts a current and a previous heartbeat period of an N-best list based on β and α for a time value t, for comparison to FIGS. 6B and 6C.

FIG. 6B depicts a current and a previous heartbeat period of an N-best list based on β and α for a time value t−1.

FIG. 6C depicts a current and a previous heartbeat period of an N-best list based on β and α for a time value t−t* where t* is a most likely time alignment.

DETAILED DESCRIPTION

Figure 1:
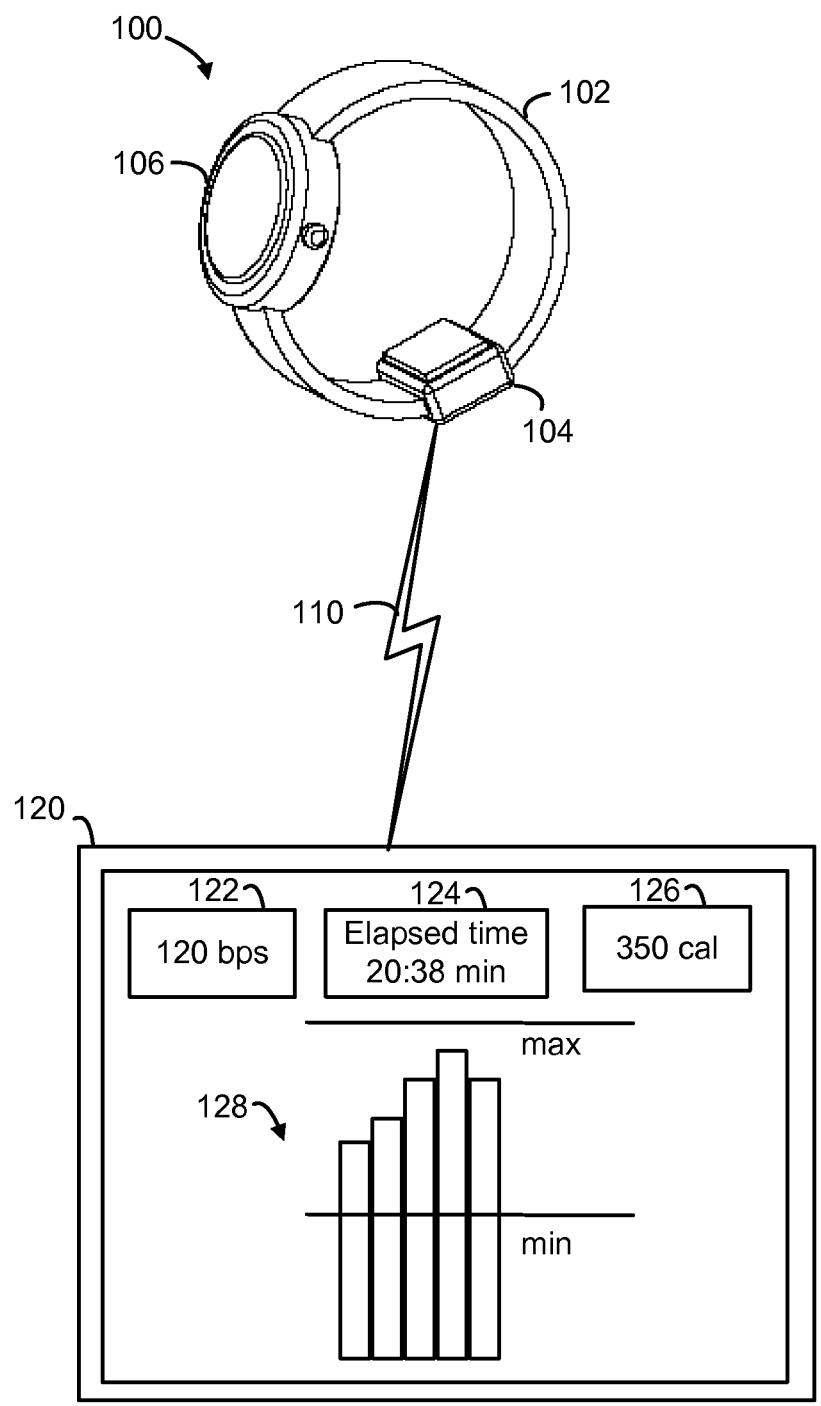
FIG. 1 depicts an example wrist-worn heart rate monitor.

FIG. 1 depicts an example wrist-worn heart rate monitor 100. The monitor 100 includes a strap 102, and, attached to the strap, a heart rate monitoring device 104 and a display device 106. The heart rate monitoring device, discussed further in connection with FIGS. 2A and 2B, detects blood flow through the radial artery at a human subject's wrist, determine the subject's heart rate based on the detected blood flow, and communicates the heart rate to the display device for display thereon. In one approach, connecting wires are molded into the strap 102 and extend between the heart rate monitoring device and the display device to allow this communication. The display device can provide an output in the form of a display of the current heart rate, for instance. An audible alarm or other output can also be provided as discussed. The display device can have the functions of a watch and stopwatch has well. In one approach, the display device has one or more control buttons which the user presses to cause the heart rate to be detected and displayed for a period of time such as a few seconds. Typically, a range of the heartbeat rate of a human is about 40-220 beats per minutes. A corresponding range of the heartbeat period is 1/40-1/220 min.

Alternatively or additionally, the heart rate monitoring device 104 transmits the heart rate via a wireless signal 110 to a remote console 120 such as a console which is mounted to a bicycle, treadmill, stair climber machine or other exercise equipment. The console can be mounted or handheld, for use by another person such as an athletic trainer or medical personnel. In this example, the console has a display with a region 122 which provides a current heart rate, e.g., 120 beats per second (bps), a region 124 which indicates a elapsed exercise time, a region 126 which indicates a number of calories burned in the exercise session, and a region 128 which is a bar chart showing a history of the heart rate, e.g., over the past few minutes, relative to a target heart rate range which is between maximum (max) and minimum (min) levels. The console can also provide an audible output such as an alarm when the heart rate moves outside the target heart rate range, to signal to the user to move faster or slower. The remote console could also be a portable device such as a cell phone, media player, personal digital assistant (PDA) or similar device. Such a device can be held in the user's hand or attached to the user's body, e.g., using a strap, or placed in a pocket of clothing worn by the user.

In addition to real-time processing and updating of a heart rate or other parameter, the heart rate monitoring device 104 can record data in a non-volatile memory such as a computer hard drive or flash memory for subsequent analysis.

Figure 2A:
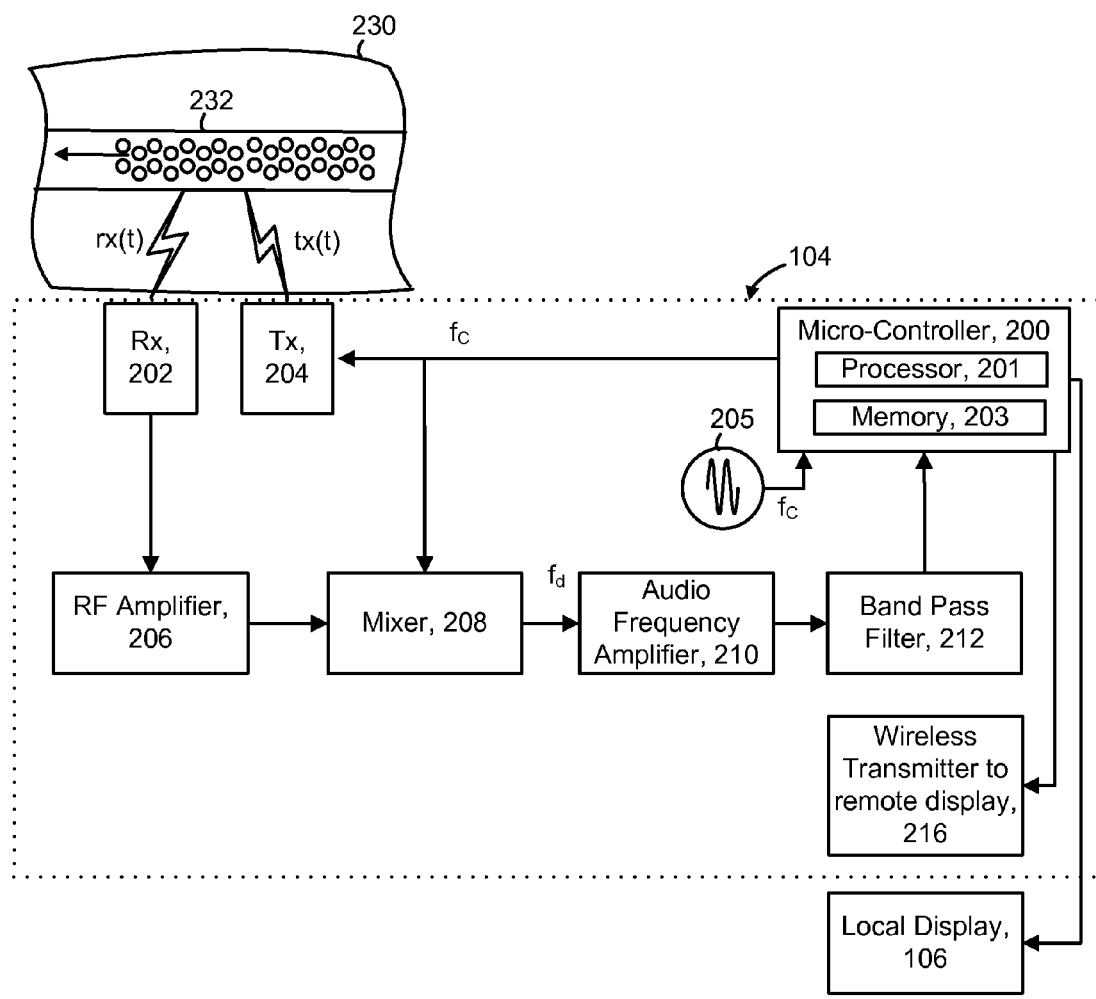
FIG. 2A depicts an example embodiment of the heart rate monitoring device 104 of FIG. 1.

FIG. 2A depicts an example embodiment of the heart rate monitoring device 104 of FIG. 1. The heart rate monitoring device can be in the form of a self-contained module which includes transducers such as ultrasonic transducers, including a transmitter (Tx) 204 which transmits an ultrasonic signal, denoted tx(t), where "t" represents time, to a subject's wrist 230, including example blood vessel 232 (such as the radial artery), and a receiver (Rx) 202 which receives a reflected ultrasonic signal, denoted rx(t), from the subject's wrist 230. While the wrist is provided as an example, other body portions may be used. The small circles in the vessel 232 represent blood which is flowing. The velocity of the flow will vary in correspondence with the heart rate. The heart rate may be defined as the number of heart contractions over a specific time period, usually defined in beats per minute. A pulse can be represented by the rhythmical dilation of a blood vessel produced by the increased volume of blood forced through the vessel by the contraction of the heart, and/or by the corresponding rhythmical change in blood velocity in the blood vessel. Since heart contractions normally produce a volume of blood that can be measured as a pulse, heart rate and pulse rate are usually the same.

The transducers can be piezoelectronic transducers, in one approach. The length of each transducer can be about one centimeter long. The transducer length is also generally equal or greater than five times its width. The frequency at which a transducer operates at is generally related to the thickness of the transducer. On example transducer is a lead zirconate-titanate transducer.

Based on an oscillator 205 whose carrier signal is passed from a microcontroller 200, the transmitter operates at a carrier frequency fc such as in an ultrasonic region of the frequency spectrum, e.g., between about 30 KHz and about 30 MHz. In one possible approach, fc is selected from a range of 1 MHz to 10 MHz. In another possible approach, fc is selected from a range of 5 MHz to 20 MHz. The carrier signal can be a sine or square wave at fc, for instance. The microcontroller 200 can be implemented as one or more of several common microcontroller integrated circuits and can include, e.g., at least one processor 201 and at least one memory 203. The at least one memory can be at least one tangible processor-readable storage device having computer readable software or code embodied thereon for programming at least one processor to perform a method for monitoring a heart rate of a subject.

The reflected ultrasonic signal is provided from the receiver 202 to an RF amplifier 206, where it is amplified, and then to a mixer 208, which demodulates the amplified signal and generates a signal with an audio range frequency, e.g., 20 Hz to 20 KHz, using the carrier signal at fc. In an example implementation, the audio range frequency is in a 4 KHz bandwidth of 20 Hz to 4 kHz. The mixer 208 can be implemented as one or more of several common mixer ICs or frequency modulation ICs, and demodulates out the carrier signal fc. The audio range signal output from the mixer at the baseband received Doppler shifted frequency fd is amplified at an audio frequency amplifier 210, then filtered at a band pass filter 212, comprising a high filter and a low pass filter. The Doppler frequency shift is due to movement of the vessel 232 and/or blood flow in the vessel. The signal output from the band pass filter 212 is provided to the microcontroller 200 for processing to determine the heart rate. In one approach, the microcontroller 200 obtains velocity samples from the signal. The velocity samples are processed to provide a signal which represents the heart rate to a wireless transmitter to a remote display 216 and/or to the local display 106.

Figure 2B:
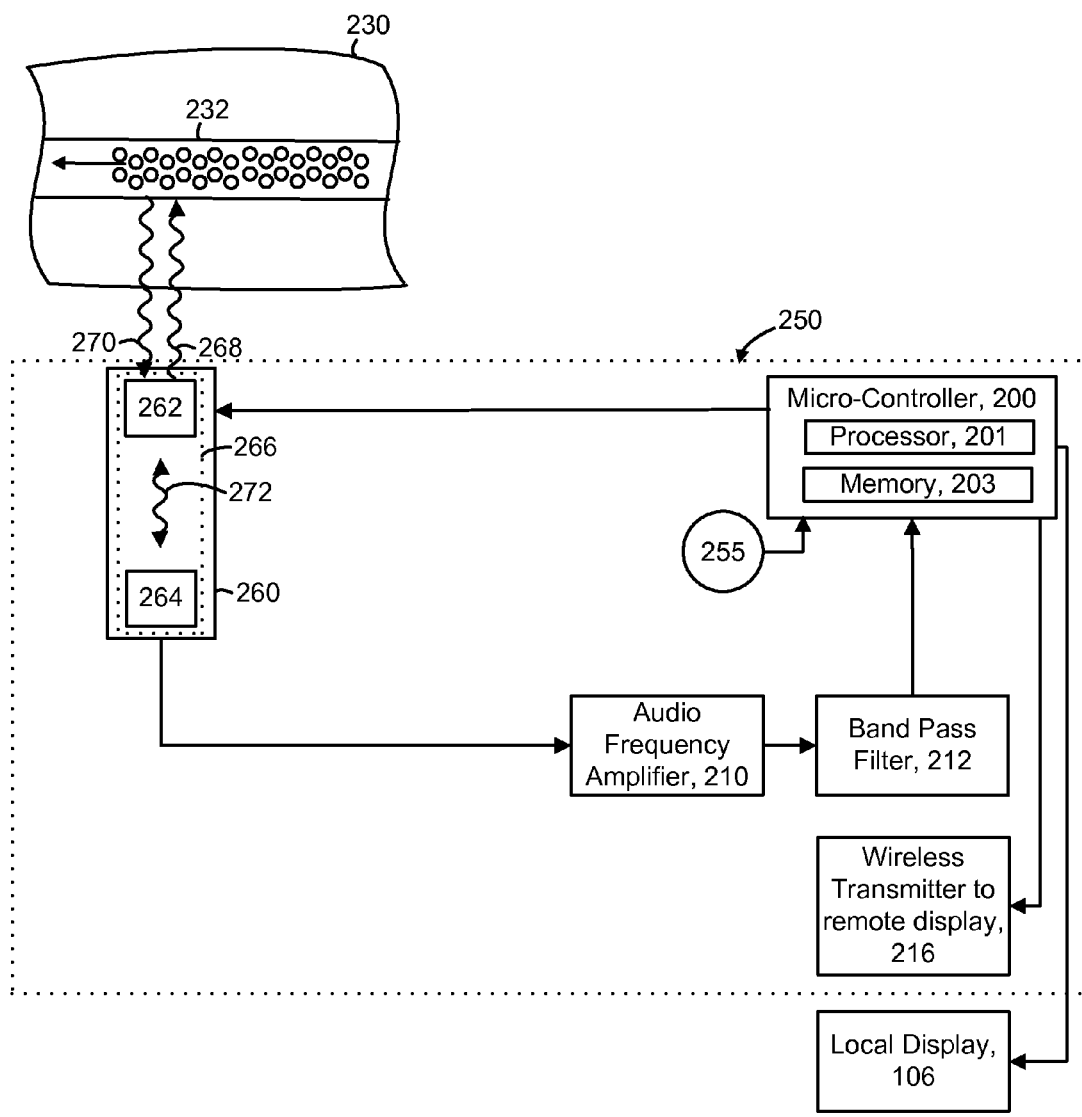
FIG. 2B depicts an example embodiment of the heart rate monitoring device 104 of FIG. 1 which uses a laser signal.

FIG. 2B depicts an example embodiment of the heart rate monitoring device 104 of FIG. 1 which uses a laser signal. Although ultrasonic Doppler signals are used in the above example, other signals can be used for heart rate monitoring.

The bandwidth of the Doppler frequency in a laser embodiment falls in the same range of the ultrasound Doppler. The self-mixing semiconductor laser diode advantageously does not need a mixer circuit. That is a significant difference from ultrasound Doppler hardware. Usually, an optical mixer is bulky and not practical for commercial use. Using a semiconductor laser diode with self mixing can allow the size of the circuitry to be reduced substantially. The sound recognition algorithms as described herein can be readily applied to laser Doppler signals as well.

Here, a heart rate monitoring device 250 includes a laser emitter diode package 260 which, in turn, includes a laser emitter diode 262 and a monitor photodiode 264 within a laser cavity 266 having a gain medium. The laser emitter diode package may be powered by a current source 255 such as a laser pump that is modulated by the micro-controller 200, e.g., to provide current as a triangle wave. In response to the current, a standing wave is created in the cavity to cause the laser emitter diode to emit a laser beam 268 toward the subject's wrist 230, for instance. The emitted light may be, e.g., infrared light in a range of 0.74 um-300 um or light in a range of 600-950 nm. A portion of the laser beam is reflected as reflected light 270 and returns to the laser cavity, where it self-mixes with the original laser signal that is also within the cavity. The monitor photodiode senses the mixed laser signal 272, converting light amplitude into an output electric signal. As the reflected light enters the cavity, the power output of the emitted beam 268 fluctuates because of the self-mixing effect and generates a beat signal. The beat signal frequency is used to determine the velocity of the blood flow and/or the blood vessel. That is, the laser signal in the cavity will have amplitude fluctuations with a frequency equal to the Doppler shift of the laser reflections. Similarly, the electrical signal which is output from the monitor photodiode can be in an audio band, and can have the amplitude fluctuations with the frequency equal to the Doppler shift of the laser reflections. The electrical signal which is output from the monitor photodiode can be processed as discussed previously, e.g., by the audio frequency amplifier 210, band pass filter 212 and micro-controller 200. Similarly, the processing which is discussed below in connection with an ultrasound signal can be applied to a laser embodiment.

As an alternative to the use of the monitor photodiode, the velocity could be determined by monitoring a resistor of the laser pump.

In another approach, multiple lasers are used, such as a first laser which couples more strongly to the blood flow to detect the velocity of the blood flow, and a second laser which couples more strongly to the wall of the blood vessel to detect the velocity of the blood vessel wall. For example, the first laser can provide a signal in the range from 750 nm to 950 nm, and the second laser can provide a signal in the range from 600 nm to 850 nm. For further details of a laser implementation, see, e.g., US2010/0081940, titled "Laser Self-Mixing Sensors for Biological Sensing," incorporated herein by reference.

Figure 3A:
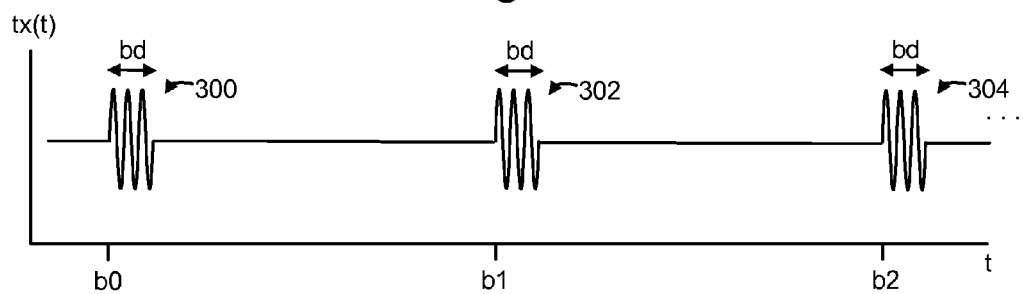
FIG. 3A depicts an example of the transmitted ultrasound signal tx(t) of FIG. 2A.

FIG. 3A depicts an example of the transmitted ultrasound signal tx(t) of FIG. 2A. In one approach, the transmitter 204 is operated in a pulsed mode, in which a burst of one or more cycles or pulses of the carrier wave are transmitted for a defined burst duration (bd). The bursts can be repeated at fixed intervals, in one approach. In this example, example bursts 300, 302 and 304 start at times b0, b1 and b2. As an example, 4,000 bursts per second (one sample every 0.25 msec.) can be used to provide an adequate time resolution of the velocity values. The transmitter could alternatively operate in a continuous mode.

Figure 3B:
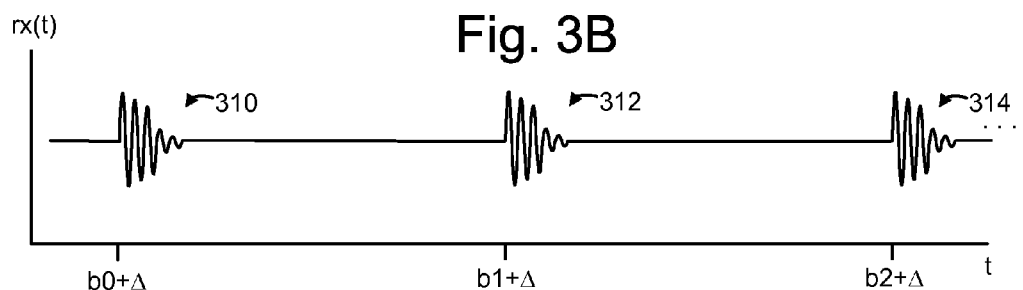
FIG. 3B depicts an example of the received ultrasound signal rx(t) of FIG. 2A.

FIG. 3B depicts an example of the received ultrasound signal rx(t) of FIG. 2A. The ultrasonic signal pulses propagate within the subject's wrist or other body portion, are reflected by the parts of the wrist which have different acoustic impedances, and return to the receiver as echo signals. The received signals are received starting at a time which is delayed by an amount from the start times t0, t1, t2 . . . . The delay Δ can be the same or different for each burst of pulses. The received signals for each burst transmission are depicted by waveforms 310, 312 and 314 which are received at b0+Δ, b1+Δ and b2+Δ, respectively. Each waveform can be converted to a velocity value, as depicted in FIG. 3C.

Figure 3C:
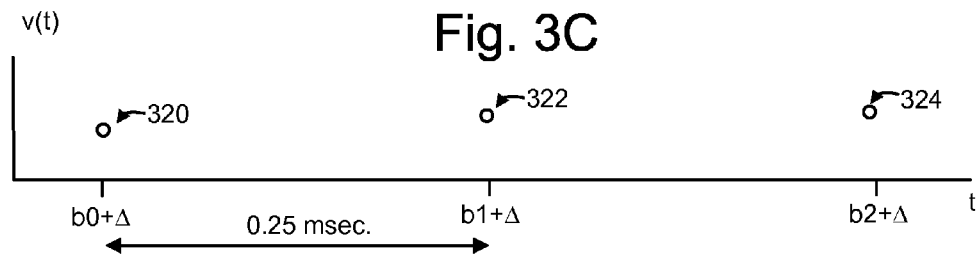
FIG. 3C depicts observations of a velocity signal based on rx(t) of FIG. 3B.

FIG. 3C depicts observations of a velocity signal based on rx(t) of FIG. 3B. Velocity values 320, 322 and 324 are calculated based on the Doppler principle from waveforms 310, 312 and 314, respectively. The time interval between the velocity values can be 0.25 msec., for instance, as mentioned. A sequence of many velocity values results in the signal v(t) of FIG. 3D.

Figure 3D:
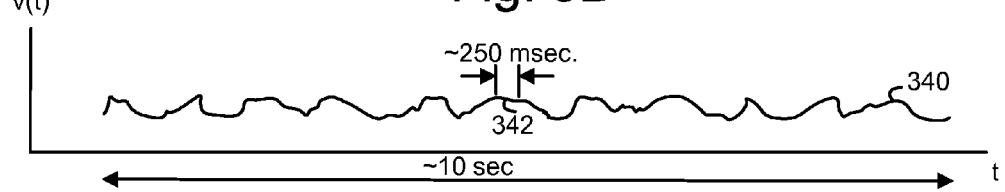
FIG. 3D depicts a velocity signal extending over several heartbeats.

FIG. 3D depicts a velocity signal 340 extending over several heartbeats, such as about ten heartbeats over ten seconds. Peaks in the signal which can be ascertained among the noise represent blood rush events of the heartbeats. An example signal portion 342 of duration 250 msec., and including 1,000 velocity values, is discussed further in connection with FIG. 4A.

FIGS. 4A-4G depicts a process for determining an instantaneous heart rate from a velocity signal such as in FIG. 3D. In one approach, techniques are provided for heart rate monitoring based on analysis of the audio-frequency Doppler modulations of an ultrasound carrier signal. A lightweight ultrasound transducer is embedded into a wearable heart-rate monitor, such as depicted in FIG. 1. Reflected signals are shifted in frequency, depending on the presence or absence of blood flow in one or more arteries which are proximate to the transducer. The received signal is modulated down to audio frequency, and the resulting audio signal is analyzed in order to track a heartbeat rate.

The following terms can be defined. A heartbeat instant can be the instant at which a blood rush event, audible in the Doppler ultrasound signal, first begins in the veins being monitored by the heart rate monitoring device. The blood rush event can be an increase in the blood velocity due to a heart contraction, for instance. For example, if we think of an ECG signal, a blood rush event can correspond to the QRS complex. For one complete heartbeat in an ECG signal, the P-wave describes the atrial contraction, the QRS complex describes the ventricular contraction and the T-wave describes the ventricular decontraction. A Q wave is any downward deflection after the P wave. An R wave follows as an upward deflection, and the S wave is any downward deflection after the R wave. Alternatively, a heartbeat instant can be any specified portion of a heartbeat period, including the start, middle or end of a heartbeat period.

A heartbeat period is the period of time that elapses between successive heartbeat instants. The heartbeat period can be the inverse of the heart rate. A cepstrum can be any acoustic feature vector, x(t), that is computed, e.g., as the discrete cosine transform (DCT) of the log spectrum of the received audio band demodulated signal at time t. In one approach, the word "cepstrum" here is intended to refer to frequency vectors computed based on Fourier spectra, frequency-warped Fourier spectra, autoregressive spectra, and/or frequency-warped autoregressive spectra.

Figure 4A:
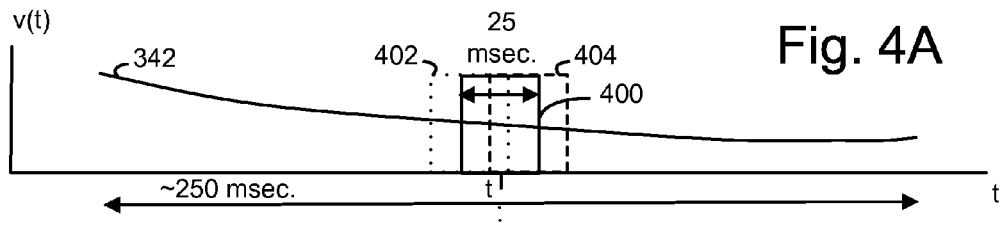
FIGS. 4A-4G depicts a process for determining an instantaneous heart rate from a velocity signal such as in FIG. 3D.

FIG. 4A depicts signal analysis windows of the portion 342 of the velocity signal of FIG. 3D, including a window 400, a previous window 402 and a subsequent window 404. The several velocity values of the signal 342 within the window 400 form an observation of v(t) are processed in FIGS. 4B-4G to obtain one heart rate value. Each window can have a duration of 25 msec. and 100 velocity values when the spacing between velocity values is 0.25 msec. Adjacent windows can overlap by 15 msec., for instance. In this case, an instantaneous heart rate value is calculated for every 10 msec. of v(t). The time axis extends over about 250 msec. or 25 centiseconds (hundredths of a second). Each window is significantly less than one heartbeat period.

In one approach to determining heart rate, a probabilistic segmentation model is used. Such a model analyzes segments of v(t) using probabilistic techniques to determine that one or more heartbeat instants are present in the segment. The timing of the heartbeat instants is then converted to a heartbeat rate. For example, an instantaneous heart rate can be determined for each signal analysis window of successive overlapping signal analysis windows.

Figure 4B:
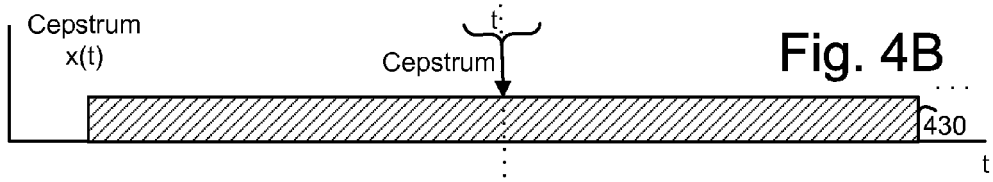

The techniques provided herein can improve the accuracy of a probabilistic segmentation model by nonlinearly transforming an extended feature vector, as follows. A cepstrum vector x(t) is computed from v(t) at time t, where t is measured, e.g., in centiseconds. For example, FIG. 4B depicts a cepstrum signal x(t) formed from the signal analysis window 400 of FIG. 4A. The cepstrum signal x(t) is depicted diagrammatically by a region 430 since x(t) is a matrix. An example approach for x(t) uses 13 different numbers per column, calculated once every 10 msec. from v(t).

The cepstrum x(t) can be obtained from the current signal analysis window 400, such as by multiplying the corresponding values/samples of v(t) by a Hamming window, determining the Fourier transform (such as the Fast Fourier Transform or FFT) of that windowed signal, taking the log magnitude of the result, and taking the discrete cosine transform (DCT) of the result. In one implementation, the log magnitude Fourier transform is compressed from 512 numbers to 32 numbers in order to represent only the spectral features audible to a human listener; this is done by adding together some of the log magnitude Fourier transforms within bands which represent the critical bands in the ear to create a lower dimensional spectrum, such as a 32-dimension spectrum which is reduced from a 512-dimension FFT. The 32-dimension frequency work spectrum is then transformed using a DCT to calculate the cepstrum.

For example, x(t) is a feature vector which is extracted from, and characterizes, a 25 msec. portion of v(t) which is in the current signal analysis window. A feature characterizes the signal from which the feature is calculated. The features of a given portion of v(t) can be compared to models of features to determine similarities. For instance, in a speech recognition system, the extracted features of an unknown utterance are compared to models of speech units such as phrases, words, syllables, phonemes and sub-phones. For example, see U.S. Pat. No. 7,464,031, titled "Speech recognition utilizing multitude of speech features," incorporated herein by reference. Similar comparisons can be made for v(t) which is also an acoustic signal.

A likelihood function $p_x(x(t))$ can be redefined to be a function of a nonlinearly discriminatively transformed vector z(t). Thus:

$$p_x(x(t)) = p_z(z(t)).$$

The discriminatively transformed vector $z(t)=[z_1(t), z_2(t), \ldots]^T$, where T represents the transpose, is composed of parameterized nonlinear functions, $$z_i(t) = g(y(t); \theta_i),$$

where $\theta_i$ is a set of learned parameters, and y(t) is an extended local observation vector created by concatenating 2M+1 consecutive local observations, $$y(t) = \begin{bmatrix} x(t-M) \\ x(t-M+1) \\ \vdots \\ x(t) \\ \vdots \\ x(t+M) \end{bmatrix}.$$

In the example of M=1, we have:

$$y(t) = \begin{bmatrix} x(t-1) \\ x(t) \\ x(t+1) \end{bmatrix}.$$

Here, x(t-1) refers to the cepstrum based on the 100 velocity values of the window 402, x(t) refers to the cepstrum based on the 100 velocity values of the window 400 and x(t+1) refers to the cepstrum based on the 100 velocity values of the window 404.

Figure 4C:
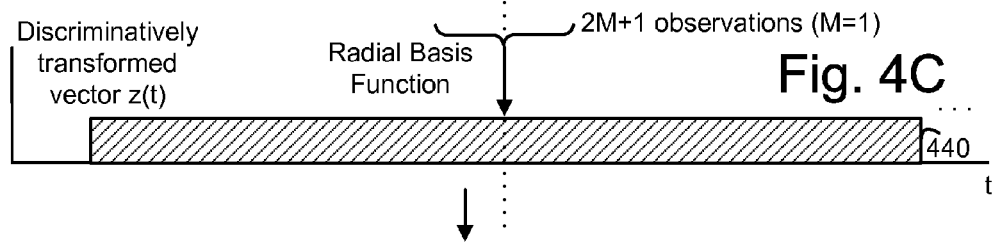

The discriminatively transformed vector z(t) is depicted in FIG. 4C as formed from the cepstrum 430 of FIG. 4B. The discriminatively transformed vector z(t) is depicted diagrammatically by a region 440. In this example, M=1, so that 2M+1=3 local observations (observations of windows 402, 400 and 404) are concatenated. z(t) is computed from the cepstra x(t−M), x(t+M). For example, with M=1, z(t) is computed from the cepstra x(t−1), x(t), x(t+1). The discriminatively transformed vector z(t) is computed from y(t)=[x(t−M), . . . , x(t+M)] according to the following formula:

$$z_i(t) = \Sigma_{q=1}^{Q} a_{iq} K(y(t), \mu_{iq})$$

where $\theta_i = \{Q, a_{i1}, \mu_{i1}, \ldots, a_{iQ}, \mu_{iQ}\}$ is the set of trainable parameters governing the $i^{th}$ component, $z_i(t)$, of the output vector z(t), and where K(y,μ) is a nonlinear kernel function whose form is chosen prior to training of the model. For example, in one implementation, K(y,μ) is a radial basis function (RBF) defined by the equation $K(y,\mu) = \exp(-|y-\mu|^2)$, and the parameters $\theta_i$ are chosen as described below in order to minimize a mean-squared error (MSE) term defined by $\Sigma_{t=1}^{NT} |c(t) - z(t)|^2$; in this case the transform is called an RBF neural network. For example, see U.S. Pat. No. 7,577,626, titled "Multi-scale radial basis function neural network," incorporated herein by reference. In another implementation, K(y,μ) is a sigmoidal function, defined by $K(y,\mu) = 1/\exp(-y^T, \mu)$, and the parameters $\theta_i$ are chosen to minimize MSE; in this case the transform is called a feed forward sigmoidal neural network. In another implementation, K(y,μ) is an RBF, but ϵ takes the form of a hinge loss error term defined by $\Sigma_{t=1}^{NT} \max(0, 1 - c(t)^T z(t))$; in this case the transform is called a support vector machine (SVM). See, e.g., US2009/0171868, titled "Method and Apparatus for Early Termination in Training of Support Vector Machines", incorporated herein by reference.

In one approach, the transformation parameters $\theta_i$ may be trained by the use of labeled training data. For example, FIG. 4K depicts example training data for one heartbeat period, including data 490 for a blood rush event, data 492 for muscle static and data 494 for silence. Muscle static can represent noise from muscle movement, such as the arm contacting the body. A set of training frames may be labeled with codes representing different perceptually distinguishable acoustic events, for example the code $c(t)=[1, 1, 0]^T$ might represent the blood rush event, the code $c(t)=[0, -1, 1]^T$ might represent the muscle static, and the code $c(t)=[-1, 0, -1]^T$ might represent the silence. Discriminative classifiers may then be trained in order to minimize an error metric $\epsilon$, by the following equation:

$$\{\theta_1, \theta_2, \theta_3\} = \arg\min \sum_{t=1}^{NT} \varepsilon(c(t), z(t))$$

where NT is the number of frames in the training data, and $\epsilon(c(t), z(t))$ is a non-negative, monotonically non-decreasing function of $|c(t)-z(t)|$.

In another aspect, the instantaneous heart rate is computed based on a dynamic programming algorithm whose search space is the set of possible heartbeat instants. The dynamic programming algorithm can maintain three lists, LL(n,t), D1(n,t), and D2(n,t). The (n,t) entry or element in each list is a real number, specifying information about the nth-most probable sequence of heartbeat instants that ends with a heartbeat instant at time t. Two of the lists, D1(n,t) and D2(n,t), specify, in centiseconds, the two most recent heartbeat periods in the candidate heartbeat sequence. Thus, the candidate heartbeat sequence includes heartbeat instants at times t−D1(n,t)−D2(n,t), t−D1(n,t), and t. The remaining list, LL(n,t), specifies the log probability that the cepstral sequence (x(1), . . . , x(t)) was generated by a sequence of heartbeats ending with three heartbeats at times t−D1(n,t)−D2(n,t), t−D1(n,t), and t, respectively. The lists are maintained sorted, so that LL(n,t)>LL(n+1,t) for all 1≤n<N. N is the number of entries in the list. An example uses N=1,000. Using two previous heartbeats (Nphb, an integer number greater than or equal to one) is an example implementation which has worked well. The list could use from one to four previous heartbeats, for instance (1≤Nphb≤4). The use of three or four previous heartbeats can result in a solution which is too computationally intense, while the use of only one previous heartbeat may result in a solution which is not sufficiently accurate.

The log likelihood LL(n,t) can be computed using an N-best dynamic programming search, as follows. For each heartbeat period $\tau$ in the range Dmin≤$\tau$≤Dmax, for each heartbeat sequence in the range 1≤b≤N, (where b is an index of an element in the list) the log probability of a candidate heartbeat sequence ending with heartbeat instants at t−$\tau$ and at t is computed as:

$LL(\text{candidate})=LL(b,t-\tau)+\alpha+\beta$, where $\alpha$ is the log probability of heartbeat period $\tau$ conditional on the two previous heartbeat periods D1(b,t−$\tau$) and D2(b,t−$\tau$), according to the following equation:

$\alpha=\ln p_\tau(\tau|D1(b,t-\tau),D2(b,t-\tau))$, where ln denotes the natural logarithm. In one implementation, $\alpha$ is computed as described below in eqn. (2). $\beta$ is the log probability of the sequence of acoustic features from t−$\tau$+1 to t being generated by a heartbeat period that begins at t−$\tau$ and ends at t, according to the following equation:

$\beta=\ln p_z(z(t-\tau+1), \ldots, z(t)|t-\tau, t)$.

This is the probability of the sequence of feature vectors z from time t−$\tau$+1 to t, conditional upon the heartbeat period beginning at time t−$\tau$+1 and ending at time t, taking the natural logarithm.

Figure 4D:
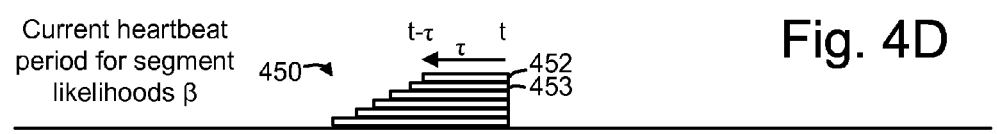

Specifically, FIG. 4D depicts candidate current heartbeat periods $\tau$ used to determine segment likelihoods $\beta$ from the discriminatively transformed vector z(t) of FIG. 4C. $\beta$ is the probability of the data (z(t)) given a candidate heartbeat period. As mentioned, as an example, 100 different values of $\tau$ can be used for a window. A few bars 450 which represent a few values of $\tau$ are depicted for simplicity. For example, one bar 452 represents one value of $\tau$ and another bar 453 represents another value of $\tau$. The magnitude of the likelihood is not depicted here. See FIG. 4H, which depicts an example of the segment likelihood $\beta$ of FIG. 4D for different values of $\tau$.

Figure 4E:
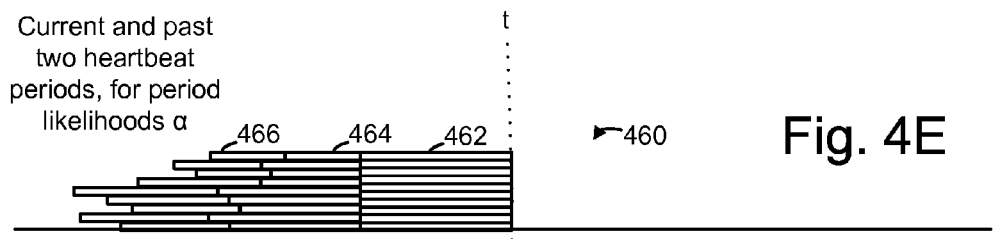
Figure 4F:
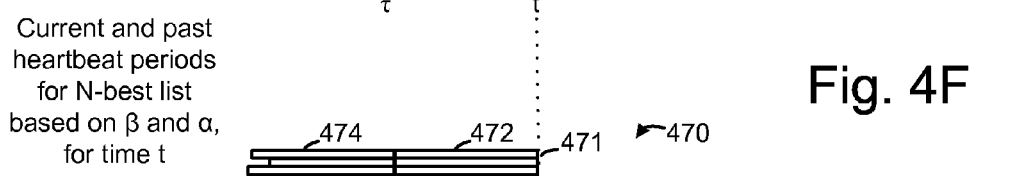

$\tau$ is a candidate heartbeat period for the current signal analysis window, and extends from t−$\tau$ to t. Note that the time scale of FIGS. 4D-4F is on the order of magnitude of a heartbeat and therefore covers a larger period of time than the time scale of FIGS. 4A-4C and 4G which is on the order of magnitude of a several analysis windows. The time "t" is the same in FIGS. 4D-4F. It is the most recent time for which we have data in FIG. 4C.

For any particular value of t, many candidate values of $\tau$ are considered. $\tau$ can be any value within a defined range of values which are prior to t. The range can be the range of all possible heartbeat durations, from Dmin (e.g., 0 or 1/220 min.) to Dmax (e.g., 1/40 min.) t is the synchronization value of the search process. Thus, at the value of t for a signal analysis window, we calculate the likelihood $\beta$ for all of the different possible values of $\tau$. For any time t of a signal analysis window, we calculate $\beta$ in FIG. 4D, $\alpha$ in FIG. 4E and the N-best list in FIG. 4F. As t moves forward in time in each new analysis window, these calculations are repeated.

FIG. 4E depicts example current and two previous heartbeat periods used to determine period likelihoods $\alpha$. $\alpha$ represents a period likelihood, which is the probability of the current heartbeat period $\tau$ given the two heartbeat periods that came before it. The two heartbeat periods are first and second previous heartbeat periods. For each of the combinations, each first previous heart beat period is directly before the candidate current heartbeat period, and each second previous heart beat period is directly before the first previous heartbeat period. $\alpha$ is based on different combinations of the first and second previous heartbeat periods.

We assume that $\tau$ is a random variable whose distribution depends on D1 and D2. We take the different possible two period sequences leading up to time $\tau$ and from each sequence, calculate the probability of getting a heartbeat going from t−$\tau$ to t given those two previous heartbeats. For simplicity, the depiction provided is for one value of $\tau$ as an example, with a few different values of D1 and D2. For example, in the set of bars 460, the bar 462 denotes the duration $\tau$, the bar 464 denotes D1 and the bar 466 denotes D2. See also FIG. 4I, which depicts an example of the period likelihood $\alpha$ of FIG. 4E for different values of $\tau$, a first prior heartbeat period D1 and a second prior heartbeat period D2. A different 2 d surface is provided for each $\tau$.

From FIGS. 4D and 4E, $\beta$ and $\alpha$ are combined to create the N-best list of FIG. 4F.

FIG. 4F depicts a current and a previous heartbeat period of an N-best list for a time value of t, based on $\beta$ and $\alpha$. The N-best list includes LL(n,t), D1(n,t) and D2(n,t). Example horizontal bars 470 include a row 471 in which a bar 472 represents the current heartbeat period and a bar 474 represents the previous heart beat period. The N-best list takes the best combinations of $\beta$ and $\alpha$ to calculate the probability of a period from t−$\tau$ to t. We keep the N-best of these combinations, such as the best 1,000 combinations. In FIG. 4E, there are 1,000 different possible combinations leading up to time t−$\tau$. We look at all of the different possible values of $\tau$ so the number of different possible combinations of $\beta$ and $\alpha$ is much more than 1,000. A pruning process occurs. We take the 1,000 possible predecessors to any given τ to determine 1,000 possible values of LL(n,t–τ), matched with 1,000 different values of α (computed from D1(n,t–τ) and D2(n,t–τ)), corresponding to that one value of τ. These 1,000 different possible combinations are evaluated for each of the different possible values of τ. Thus, for example, if there are 100 different possible values of τ, then there are 100×1,000=100,000 different possible values of LL(n,t–τ)+α+β to be computed at each t. From those combinations, we choose the 1,000 best for the time point t of the current signal analysis window.

In particular, the search candidate LL (candidate) is then compared to the least likely previously stored candidate at time t, which is LL(N,t). If LL(N,t)<LL (candidate), then LL (candidate) is sorted into the LL list. The D1 and D2 lists are updated at the same time, in order to make sure that the three lists remain synchronized.

The instantaneous heart rate is computed by finding the most likely time alignment of the heartbeat, then averaging the two recent heartbeat periods, for instance. The most likely time alignment is given by:

$$t^*(t) = \arg\max\{LL(1,t-D\max), \ldots, LL(1,t)\},$$

where Dmax is the largest plausible heartbeat period. The notation "t*" denotes the most likely alignment in units of time, and is between t and t–Dmax. For instance, with forty beats per minute as the lowest plausible heart rate, Dmax=1/40 min. The instantaneous heart rate estimate is then given by:

$$R(t) + \frac{2}{D1(1, t^*(t)) + D2(1, t^*(t))}.$$

Figure 4G:
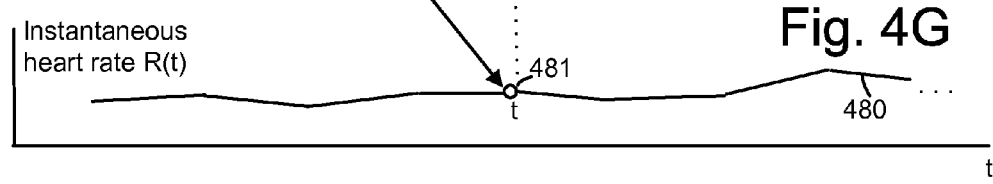

FIG. 4G depicts an instantaneous heart rate 480 formed from the N-best list of FIG. 4F. The rate is for the time t as indicated at circle 481, at the center of the signal analysis window 400. R(t) can similarly be determined at other time points, for other signal analysis windows. The most probable heart rate estimate for R(t) can be obtained from the time of the current heart beat estimate based on the best score of FIG. 4F, and the corresponding times of the two previous heart beats. From these three heart beat times, two heart beat periods are determined. From this, an average heart beat period is determined from the sum of the two heart beat periods divided by two, and, from this, R(t) is the inverse of this average heart beat period.

In an example implementation, every 10 msec., we look for the best possible alignment leading up to t. The model assumes we detect each successive heart beat. We can look at the last 0.5-1 sec. or so, which is a reasonable heart beat period and look for the best alignment of a heart beat within that time period, and calculate the heart beat period leading up to that most recent heartbeat. We start at t and go back, looking though the sequence of N-best lists for all possible values of t leading up to the current t, in the past second or so, and once we find the best of the best within that segment, we take the inverse of that heartbeat period. Thus, we look for the best possible alignment and the best possible heart beat period leading to that alignment.

In sum, β indicates the probability of z(t) given a particular heart beat period, based on training data which indicates what a full heart beat period looks like acoustically. The training data can be generic to a human, or can be classified by factors such as age and gender, or even specific to a person. A series of Gaussian mixture models (e.g., as defined in connection with eqn. (5) below) calculates the probability that a portion of the received acoustic signal (e.g., the current signal analysis window of v(t)) matches, e.g., sounds like, a full heart beat period of the training data. α indicates the probability of getting a particular heart beat period given the previous two heart beat periods. The predictive model assumes it is likely that the heart beat will change relatively slowly from one period to the next. This is a predictive model which says, e.g., if the two previous heart beat periods were one second, then the current heart beat period is likely to be one second. An outcome which varies from this is relatively less likely.

Further, a method is provided for efficiently estimating $\alpha = p(\tau|D1, D2)$, the probability of sequential heartbeat periods, in a fashion suitable for temporally sequential dynamic programming. The probability of a heartbeat duration τ is modeled in terms of a dynamic model, $\mu(D1, D2)$, and a perturbation model, $p_v(v|D1, D2)$, defined as follows. First $\mu(D1, D2)$ is defined to be a conditional estimate of the expected log heartbeat period:

$$E[\ln \tau | D1, D2] = \mu(D1, D2) \tag{1}$$

Second, $p_v(v|D1,D2)$ is a model of the probability density function of the random variable V, where E[V]=0. For example, $p_v(v)$ may be a Gaussian probability density with conditional variance $\sigma^2(D1,D2)$. Finally, the conditional probability density function of heartbeat period τ is given by:

$$\alpha = p_\tau(\tau|D1,D2) = p_v(\ln \tau - \mu(D1,D2)|D1,D2) \tag{2}$$

A method is provided for efficiently estimating $p_z(z(t-\tau+1), \ldots, z(t)|t-\tau, t)$, the probability of the acoustic signal given knowledge of heartbeat times, in a sequential fashion suitable for temporally sequential dynamic programming.

Define $t_R$ to be the duration, in frames, of a standardized heartbeat model stored in memory. Define q(s) to be a non-negative, monotonically non-decreasing time-warping function which warps the candidate heartbeat period t–τ+s, for $1 \le s \le T$, so that it matches the reference duration $t_R$. In particular, the endpoints of q(s) are given by q(1)=1 and $q(\tau)=t_R$. Define $p_Q(Q|\tau)$ to be a model of the probability of the warping function $Q=[q(1), \ldots, q(\tau)]$. For example $p_Q(Q)$ may be a probability density function defined over the set of all piecewise-linear warping functions, $$q(s) = b_k + a_k s \text{ for } s_{k-1} < s \le s_k, 1 \le k \le K \tag{3}$$

where $s_0 = 0$, $s_K = \tau$, and the coefficients $a_k$, $b_k$ are pre-computed so that q(s) contains no discontinuities. In order to compute the probability of the function q(s) given in Eq. 3, the following probability table is stored in memory (e.g., memory 203 in FIG. 2A):

$$p_Q(Q) = p(s_1, \ldots, s_{K-1}|s_0=0, s_K=\tau), \tag{4}$$

Define $p_z(z(s)|q(s))$ to be a model of the probability density function of the acoustic feature vector z(s) given the reference time q(s). For example, $p_z(z(s)|q(s))$ may be a piece-wise mixture Gaussian probability density function, $$p_z(z(s)|q(s)) = \Sigma_{m=1}^M c_{km} N(z(s); \mu_{km}, \Sigma_{km}), s_{k-1} \le s \le s_k, 1 \le k \le K, \tag{5}$$

where $N(z(s); \mu_{km}, \Sigma_{km})$ is the multivariate Gaussian probability density function with mean vector μ and covariance matrix Σ evaluated at measurement vector z. In order to parameterize $p_z(z)$ as shown in Eq. 5, the following parameters are stored in memory: K×M scalar mixture weights $c_{km}$, K×M mean vectors $\mu_{km}$, and K×M covariance matrices $\Sigma_{km}$.

The log probability β corresponding to any given t and τ is then computed using either of the following two probabilistic acoustic models. These are two different dynamic programming algorithms. A first model is a soft-alignment model based on the following equation:

$$\beta = \ln\{p(z(t-\tau+1), \ldots, z(t)|t-\tau, t)\} = \ln\{\Sigma_Q p_Q(Q|\Sigma) \Pi_{s=1}^\tau p_z(z(t-\tau+s)|q(s))\}$$

For example, see U.S. Pat. No. 7,505,950, titled "Soft alignment based on a probability of time alignment," incorporated herein by reference. A second model is a forced-alignment model based on the following equation:

$$\beta = \ln\{p(z(t-\tau+1), \ldots, z(t)|t-\tau, t) =$$

$$\ln\left\{\underset{Q}{\operatorname{argmax}}\, p_Q(Q|\tau)\prod_{s=1}^{\tau} p_Z(z(t-\tau+s)|q(s))\right\}$$

For example, see U.S. Pat. No. 7,216,079, titled "Method and apparatus for discriminative training of acoustic models of a speech recognition system," incorporated herein by reference.

Figure 4H:
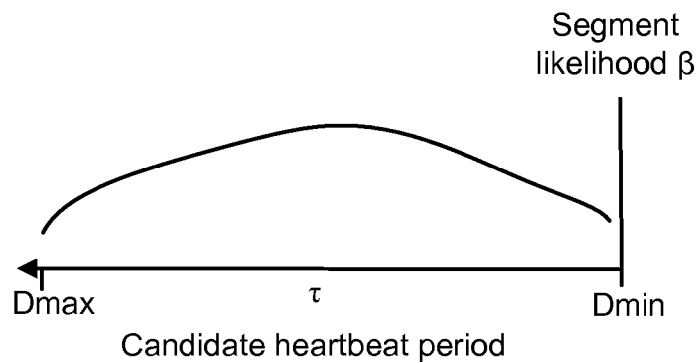
FIG. 4H depicts an example of the segment likelihood $\beta$ of FIG. 4D for different values of $\tau$.
Figure 4I:
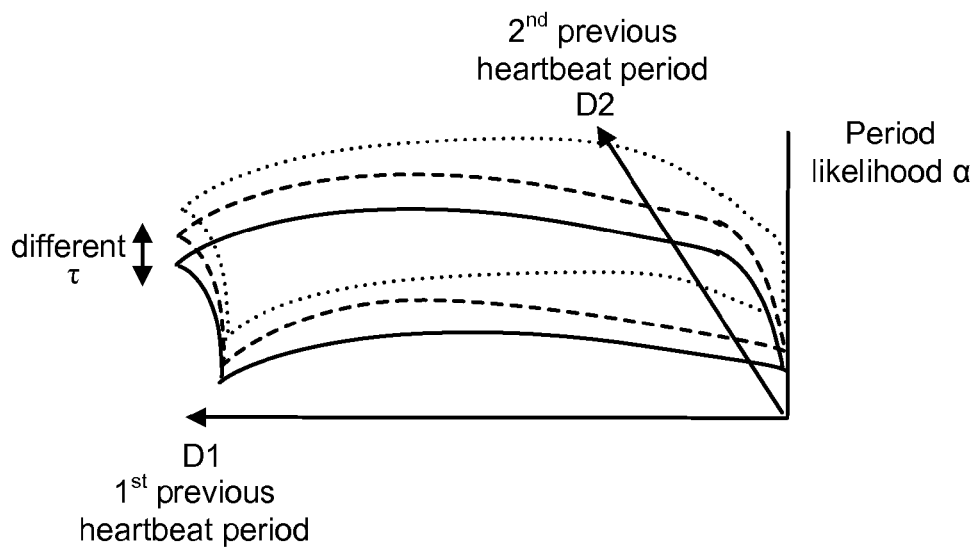
FIG. 4I depicts an example of the period likelihood $\alpha$ of FIG. 4E for different values of $\tau$, a first prior heartbeat period D1 and a second prior heartbeat period D2.

These involve different alignments up to the nodes in FIG. 4H. We have a piece-wise linear alignment between the reference heartbeat model and the observed heartbeat durations. The difference between the models involves whether any one of the nodes is computing by calculating the summation over all possible previous node times (model 1), or the maximum over all possible previous node times (model 2).

FIG. 4J depicts a piece-wise linear mapping from the time axis of the signal, $1 \leq s \leq \tau$, to the time axis of the reference heartbeat model, $1 \leq q(s) \leq t_R$. This is part of the computation of $\beta$. Any given heartbeat duration is variable in time. The x-axis is a time scale of a heart beat duration extending between 1 and $\tau$ which corresponds to a time between $\tau$ and t in FIG. 4D. The arbitrary heart beat duration is normalized to a fixed reference duration, on the y-axis, between 1 and $t_R$ to calculate $\beta$.

Figure 5A:
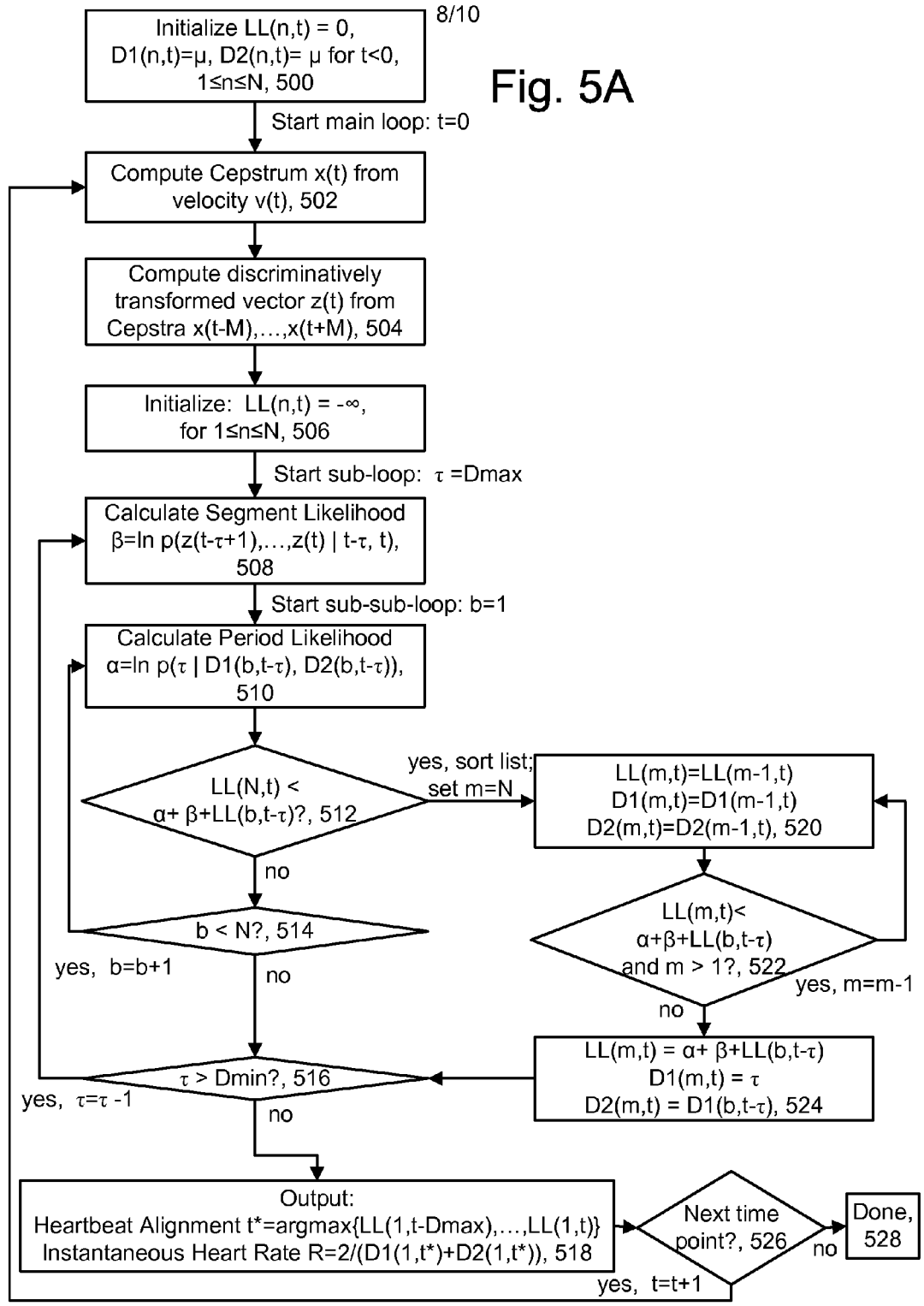
FIG. 5A depicts a flowchart of a method for determining an instantaneous heart rate, corresponding to FIGS. 4A-4G.

FIG. 5A depicts a flowchart of a method for determining an instantaneous heart rate, corresponding to FIGS. 4A-4G. Step 500 initializes the three lists, LL(n,t)=0, D1(n,t)µ, and D2(n, t)=µ for the dynamic programming algorithm. For all negative times (t<0), we initialize LL(n,t)=0, which means that all likelihoods are equally likely.

A main loop is then started with t=0. Each main loop represents processing of one signal analysis window. Step 502 computes the cepstrum x(t) from v(t). Step 504 computes the discriminatively transformed vector z(t) from the cepstra c(t−M), . . . , x(t+M). Step 506 initializes LL(n,t)=−∞ for $1 \leq n \leq N$. Next, a sub-loop starts with τ=Dmax. Setting LL(n, t)=−∞ is a placeholder until a candidate heartbeat duration is available. LL(n,t)=−∞ is less than any new candidate coming in. This gets replaced in the sort list (step 524) by α+β+LL (b,t−τ).

Step 508 calculates the segment likelihood β=ln p(z(t−τ+1), . . . , z(t)|t−τ, t). This can be considered to be determining a first set of probabilities β by determining probabilities of different current heartbeat periods, based on the features z(t).

Next, a sub-sub-loop starts with a loop index b set to one. b is an index into the previous N-best list.

Step 510 calculates the period likelihood α=ln p(τ|D1(b, t−τ), D2(b,t−τ)). This can be considered to be determining a second set of probabilities α by determining probabilities of the different current heartbeat periods, based on an integer number Nphb>0 (e.g., Nphb=2) of different previous heartbeat periods.

Decision step 512 determines whether LL(N,t)<α+β+LL (b,t−τ). If decision step 512 is true, the list is sorted and the index m is initialized to N. LL(n,t) is the N-best list at time t. LL(b,t−τ) is the N-best list at time t−τ.

Specifically, step 520 sets LL(m,t)=LL(m−1,t), D1(m,t)= D1(m−1,t) and D2(m,t)=D2(m−1,t). D1 and D2 are sorted so that each element in their list corresponds to a corresponding element in LL(n,t). So, it is not true that D1(m,t)≥D1(m+1,t).

There is a correspondence between any given element of LL and a corresponding element of D1 and D2 so that, once LL is sorted, D1 and D2 are sorted correspondingly.

Decision step 522 determines whether LL(m,t)<α+β+LL (b,t−τ) and m>1. If decision step 522 is true, m is decremented by one and step 520 is repeated. If decision step 522 is false, the lists are updated in step 524 by setting LL(m,t)=α+β+LL (b,t−τ), D1(m,t)=τ and D2(m,t)=D1(b,t−τ). Subsequently, decision step 516 determines whether T>Dmin. If decision step 516 is true, τ is decremented by one time unit (e.g., 0.01 sec) and the control flow returns to step 508. If decision step 516 is false, step 518 provides an output by determining the heartbeat alignment t*=argmax{LL(1,t−Dmax), . . . , LL(1, t)} and the resulting Instantaneous Heart Rate R=2/(D1(1, t*)+D2(1,t*)). The alignment t* takes the highest score from among the best matches. See also FIGS. 6A-6C. Next, if there is a next time point, e.g., a next signal analysis window, to process at decision step 526, t is incremented by one time unit (e.g., 0.01 sec) and the control flow returns to step 502 to process the next signal analysis window. If there is no next time point to process at decision step 526, the process is done is at step 528.

If decision step 512 is false, decision step 514 determines whether b<N. If decision step 514 is true, b is incremented by one and the control flow returns to step 510. If decision step 514 is false, decision step 516 is reached, as discussed.

Figure 5B:
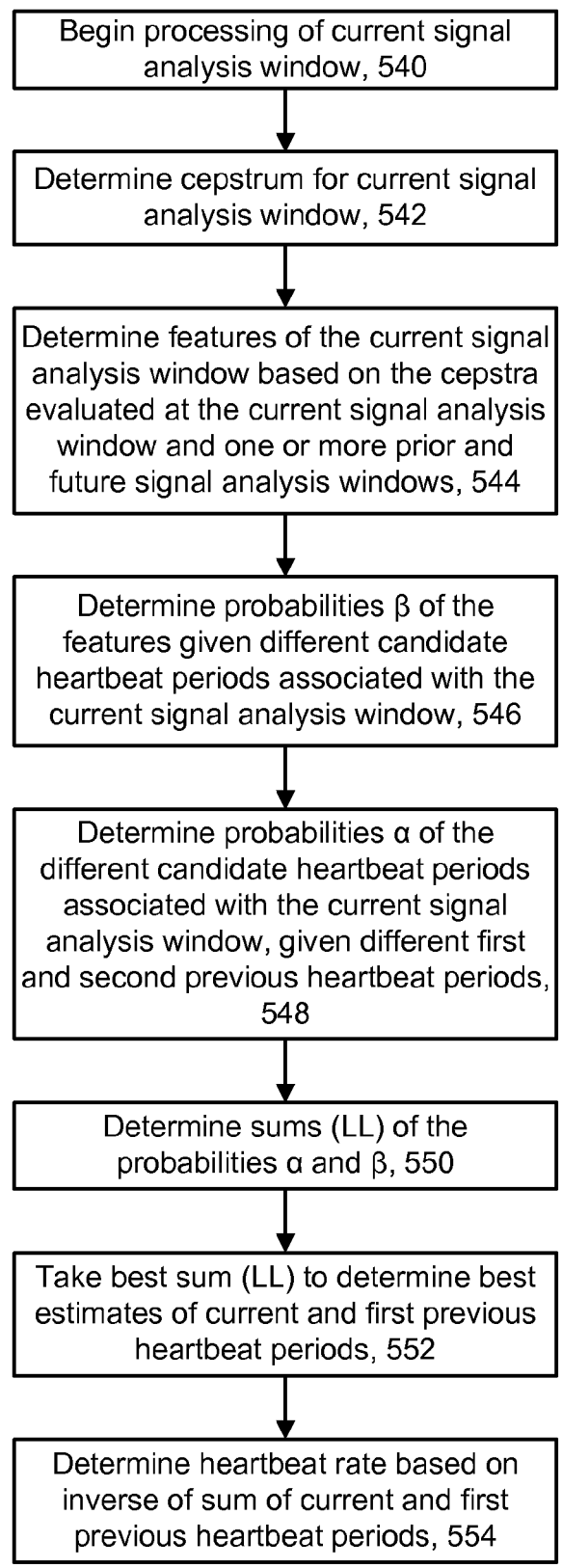
FIG. 5B depicts a generalization of the method for determining an instantaneous heart rate of FIG. 5A.

FIG. 5B depicts a generalization of the method for determining an instantaneous heart rate of FIG. 5A. Step 540 begins processing of the current signal analysis window. Step 542 determines a cepstrum for the current signal analysis window. Step 544 determines features of the current signal analysis window based on the cepstra evaluated at the current signal analysis window and one or more prior and future signal analysis windows. Step 546 determines probabilities β of the features given different candidate heartbeat periods associated with the current signal analysis window. Step 548 determine probabilities α of the different candidate heartbeat periods associated with the current signal analysis window, given different first and second previous heartbeat periods. Step 550 determines sums (LL) of the probabilities α and β. Step 552 takes a best sum (LL) to determine best estimates of current and first previous heartbeat periods. Step 554 determines a heartbeat rate based on inverse of sum of current and first previous heartbeat periods.

FIG. 6A repeats FIG. 4F, which depicts a current and a previous heartbeat period of an N-best list based on β and α for a time value t, for comparison to FIGS. 6B and 6C. As mentioned, an N-best list can be obtained for each of the different time values t, t−1, t−2, . . . .

FIG. 6B depicts a current and a previous heartbeat period of an N-best list based on β and α for a time value t−1. For one example entry on the list, bar 602 represents the current heartbeat period and bar 604 represents the previous heartbeat period.

FIG. 6C depicts a current and a previous heartbeat period of an N-best list based on β and α for a time value t−t* where t* is a most likely time alignment. For one example entry on the list, bar 612 represents the current heartbeat period and bar 614 represents the previous heartbeat period.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen to best explain the principles of the technology and its practical application to thereby enable others skilled in the art to best utilize the technology in various embodiments and with various modifications as are suited to the particular use contemplated. It is intended that the scope of the technology be defined by the claims appended hereto.

I claim:

1. At least one non-transitory tangible processor-readable storage device having computer readable software embodied thereon for programming at least one processor to perform a method for monitoring a heartbeat period of a subject, the method comprising:

obtaining velocity samples from a signal reflected from a subject for successive overlapping signal analysis windows, the velocity samples comprise velocity samples v(t) for a current signal analysis window centered at a time t, velocity samples v(t−1) from a prior signal analysis window and velocity samples v(t+1) from a future signal analysis window, the velocity samples obtained from the signal represent a velocity of blood flowing in the subject, and each window is shorter than the heartbeat period of the subject;

determining a cepstrum x(t) of the velocity samples v(t), a cepstrum x(t−1) of the velocity samples v(t−1) and a cepstrum x(t+1) of the velocity samples v(t+1);

providing a vector y(t) comprising x(t−1), x(t) and x(t+1);

determining a vector z(t) by nonlinearly transforming the vector y(t);

defining different heartbeat periods τ that begin at t−τ and end at t;

for each heartbeat period τ of the different heartbeat periods: determining a probability β of the vector z(t), and determining a probability α that the heartbeat period τ is the heartbeat period of the subject given one or more previous heartbeat periods of the subject; and determining which of the heartbeat periods τ is most probable, based on the probabilities β and α.

2. The at least one non-transitory tangible processor-readable storage device of claim 1, wherein:

the determining the probabilities β comprises determining probabilities that the velocity samples v(t) matches heartbeat period of training data, the training data comprises at least one of a blood rush event, muscle static or silence.

3. The at least one non-transitory tangible processor-readable storage device of claim 1, wherein for each heartbeat period τ of the different heartbeat periods:

the probability α is based on different combinations of first and second previous heartbeat periods; and for each of the combinations, each first previous heart beat period is directly before the heartbeat period τ, and each second previous heart beat period is directly before the first previous heartbeat period.

4. The at least one non-transitory tangible processor-readable storage device of claim 3, further comprising:

for each heartbeat period τ of the different heartbeat periods, the determining the probability α comprises modeling each heartbeat period τ in terms of a dynamic model, μ(D1, D2), where D1 are the first previous heartbeat periods and D2 are the second previous heartbeat periods, and a perturbation model, $p_v(v|D1, D2)$.

5. The at least one non-transitory tangible processor-readable storage device of claim 4, wherein:

the dynamic model μ(D1, D2) is a conditional estimate of an expected log heartbeat period: $E[\ln \tau | D1, D2] = \mu(D1, D2)$;

the perturbation model $p_v(v|D1, D2)$ is a model of a probability density function of a random variable V, where E[V]=0; and the probabilities α are given by $\alpha = p_\tau(\tau|D1, D2) = p_V(\ln \tau - \mu(D1, D2)|D1, D2)$.

6. The at least one non-transitory tangible processor-readable storage device of claim 4, wherein:

the perturbation model $p_v(v)$ is a Gaussian probability density with conditional variance $\sigma^2(D1,D2)$.

7. The at least one non-transitory tangible processor-readable storage device of claim 1, wherein:

the vector z(t) is a discriminatively transformed vector which is obtained from the vector y(t).

8. The at least one non-transitory tangible processor-readable storage device of claim 1, wherein:

the vector z(t) is obtained using a radial basis function of: the vector y(t) and a set of trainable parameters.

9. The at least one non-transitory tangible processor-readable storage device of claim 1, wherein:

the vector z(t) is obtained using a sigmoidal function of: the vector y(t) and a set of trainable parameters.

10. A heartbeat period monitoring device for monitoring a heartbeat period of a subject, comprising:

at least one micro-controller;

at least one transmitter which transmits a signal toward a subject, responsive to the micro-controller;

at least one receiver which receives a reflection of the signal from the subject; and circuitry for down modulating the reflection of the signal, resulting in a signal in an audio frequency, responsive to the micro-controller, the at least one micro-controller:

obtains velocity samples from the signal in the audio frequency for successive overlapping signal analysis windows, the velocity samples comprise velocity samples v(t) for a current signal analysis window centered at a time t, velocity samples v(t−1) from a prior signal analysis window and velocity samples v(t+1) from a future signal analysis window, the velocity samples obtained from the signal represent a velocity of blood flowing in the subject, and each window is shorter than the heartbeat period of the subject, determines a cepstrum x(t) of the velocity samples v(t), a cepstrum x(t−1) of the velocity samples v(t−1) and a cepstrum x(t+1) of the velocity samples v(t+1), provides a vector y(t) comprising x(t−1), x(t) and x(t+1), determines a vector z(t) by nonlinearly transforming the vector y(t), defines different heartbeat periods τ that begin at t−τ and end at t, (c) for each heartbeat period τ of the different heartbeat periods, determines a probability β of the vector z(t), and determines probability α that the heartbeat period τ is the heartbeat period of the subject given one or more previous heartbeat periods of the subject, and determines which of the heartbeat periods τ is most probable, based on the probabilities β and α.

11. The heartbeat period monitoring device of claim 10, wherein:

the transmitter transmits the signal toward the subject as an ultrasound signal; and the signal reflected from the subject comprise an ultrasound signal which is down modulated to an audio signal.

12. The heartbeat period monitoring device of claim 10, wherein for each heartbeat period τ of the different heartbeat periods:
- the probability α is based on different combinations of first and second previous heartbeat periods; and
- for each of the combinations, each first previous heart beat period is directly before the heartbeat period τ, and each second previous heart beat period is directly before the first previous heartbeat period.

13. The heartbeat period monitoring device of claim 10, wherein:
- the vector z(t) is a discriminatively transformed vector which is obtained from the vector y(t).

14. A heartbeat period monitoring device for monitoring a heartbeat period of a subject, comprising:
- at least one micro-controller; and
- at least one laser emitter diode package responsive to the at least one micro-controller, the at least one laser emitter diode package comprising a laser emitter diode and a monitor photodiode in a cavity, the laser emitter diode transmits a laser beam toward a subject, the laser beam is reflected by the subject, at least in part, back into the cavity as a reflected optical signal, the reflected optical signal mixes in the cavity to provide a mixed optical signal, the monitor photodiode converts the mixed optical signal to an electrical signal, and the electrical signal is in an audio band and has amplitude fluctuations with a frequency equal to a Doppler shift of the reflected optical signal,
- the at least one micro-controller:
  - obtains velocity samples from the electrical signal for successive overlapping signal analysis windows, the velocity samples comprise velocity samples v(t) for a current signal analysis window centered at a time t, velocity samples v(t−1) from a prior signal analysis window and velocity samples v(t+1) from a future signal analysis window, the velocity samples obtained from the signal represent a velocity of blood flowing in the subject, and each window is shorter than the heartbeat period of the subject,
  - determines a cepstrum x(t) of the velocity samples v(t), a cepstrum x(t−1) of the velocity samples v(t−1) and a cepstrum x(t+1) of the velocity samples v(t+1),
  - provides a vector y(t) comprising x(t−1), x(t) and x(t+1),
  - determines a vector z(t) by nonlinearly transforming the vector y(t),
  - defines different heartbeat periods τ that begin at t−τ and end at t,
  - for each heartbeat period τ of the different heartbeat periods, determines a probability β of the vector z(t), and determines a probability α that the heartbeat period τ is the heartbeat period of the subject given one or more, previous heartbeat periods of the subject, and
  - determines which of the heartbeat periods τ is most probable, based on the probabilities β and α.

15. The heartbeat period monitoring device of claim 14, wherein for each heartbeat period τ of the different heartbeat periods:
- the probability α is based on different combinations of first and second previous heartbeat periods; and
- for each of the combinations, each first previous heart beat period is directly before the heartbeat period τ, and each second previous heart beat period is directly before the first previous heartbeat period.

16. The heartbeat period monitoring device of claim 14, wherein:
- the vector z(t) is a discriminatively transformed vector which is obtained from the vector y(t).

17. A computer-implemented method for monitoring a heartbeat period of a subject, comprising the computer-implemented steps of:
- obtaining velocity samples from a signal reflected from a subject for successive overlapping signal analysis windows, the velocity samples comprise velocity samples v(t) for a current signal analysis window centered at a time t, velocity samples v(t−1) from a prior signal analysis window and velocity samples v(t+1) from a future signal analysis window, the velocity samples obtained from the signal represent a velocity of blood flowing in the subject, and each window is shorter than the heartbeat period of the subject;
- determining a vector x(t) of spectral features of the velocity samples v(t), a vector x(t−1) of spectral features of the velocity samples v(t−1) and vector x(t+1) of spectral features of the velocity samples v(t+1);
- providing a vector y(t) comprising x(t−1), x(t) and x(t+1);
- determining a vector z(t) by nonlinearly transforming the vector y(t);
- defining different heartbeat periods τ that begin at t−τ and end at t:
- for each heartbeat period τ of the different heartbeat periods, determining a probability β of the vector z(t) and determining a probability α that the heartbeat period τ is the heartbeat period of the subject given one or more previous heartbeat periods of the subject; and
- determining which of the heartbeat periods τ is most probable, based on the probabilities β and α.

* * * * *